United States Patent
Robertson et al.

(12) 
(10) Patent No.: US 6,676,671 B2
(45) Date of Patent: *Jan. 13, 2004

(54) STAPLING APPARATUS AND METHOD FOR HEART VALVE REPLACEMENT

(75) Inventors: John Charles Robertson, Bloomfield, CT (US); Keith Ratcliff, Newtown, CT (US); Brian W. Moulder, Seymour, CT (US)

(73) Assignee: United States Surgical, Norwalk, CT (US)

( * ) Notice: Subject to any disclaimer, the term of this patent is extended or adjusted under 35 U.S.C. 154(b) by 204 days.

This patent is subject to a terminal disclaimer.

(21) Appl. No.: 09/798,827

(22) Filed: Mar. 2, 2001

(65) Prior Publication Data

US 2001/0031972 A1 Oct. 18, 2001

Related U.S. Application Data

(63) Continuation of application No. 09/391,538, filed on Sep. 8, 1999, now Pat. No. 6,203,553.
(60) Provisional application No. 60/100,300, filed on Sep. 15, 1998.

(51) Int. Cl.[7] .............................................. A61B 17/04
(52) U.S. Cl. ................... 606/139; 606/153; 227/175.1; 227/181.1
(58) Field of Search ............................... 606/139, 151, 606/153, 155; 227/19, 181.1; 623/2.1

(56) References Cited

U.S. PATENT DOCUMENTS

| | | | |
|---|---|---|---|
| 3,587,115 A | 6/1971 | Shiley | |
| 5,571,215 A | 11/1996 | Sterman et al. | |
| 5,881,943 A | 3/1999 | Heck et al. | |
| 5,964,782 A | 10/1999 | Lafontaine | |
| 5,993,468 A | 11/1999 | Rygaard | |
| 6,203,553 B1 * | 3/2001 | Robertson et al. | 606/139 |
| 6,464,707 B1 * | 10/2002 | Bjerken | 606/139 |
| 6,491,704 B2 * | 12/2002 | Gifford, III et al. | 606/153 |

* cited by examiner

*Primary Examiner*—Peter Nerbun

(57) ABSTRACT

A surgical stapler for securing a prosthetic heart valve within a patient is disclosed and generally includes a first cylindrical portion for carrying a staple assembly on a distal end thereof, a second cylindrical portion positioned concentrically about the first cylindrical portion and having a camming arm on a distal end thereof and a third cylindrical portion positioned concentrically about the second cylindrical portion and having an anvil flange on a distal end thereof, the camming arm configured to cam the staple assembly radially outward and drive the staple assembly distally such that a first leg of the staple assembly penetrates a cuff of the prosthetic heart valve and a second leg of the staple assembly pierces a portion of heart tissue surrounding the prosthetic heart valve to secure the valve. A method of installing a heart valve within a patient utilizing the surgical stapler is also disclosed.

8 Claims, 8 Drawing Sheets

STAPLING APPARATUS AND METHOD FOR HEART VALVE REPLACEMENT

This application is a Continuation of prior application Ser. No. 09/391,538 filed Sep. 8, 1999, U.S. Pat. No. 6,203,553 which claims priority from Provisional Application No. 60/100,300 filed Sep. 15, 1998.

BACKGROUND

1. Technical Field

The subject disclosure relates to minimally invasive surgical procedures and apparatus and, more particularly, to instruments and methods for performing heart valve replacement surgery.

2. Background of Related Art

The diagnosis and treatment of coronary disease and related conditions often requires repair or replacement of the valves located within the heart. Various factors, such as, for example, calcification, may result in the mitrial or aortic valves becoming impaired or functionally inoperative requiring replacement. Where replacement of a heart valve is required, in general, the dysfunctional valve is cut out and replaced with either an artificial, synthetic heart valve or a harvested porcine heart valve. The replacement valve is typically sutured in place of the original valve.

Access to the heart in a patient's thoracic cavity is achieved by making a longitudinal incision in the chest. This procedure, referred to as a median sternotomy includes cutting through the sternum and forcing the two opposing halves of the rib cage to be spread apart allowing access to the thoracic cavity and thus the heart.

Suitable instruments for spreading and holding apart the rib cage are marketed by United States Surgical Corporation, Norwalk, Conn. These instruments include, for example, Mini-CABG* retractors and related accessories. The Mini-CABG* universal retractor includes a substantially planar base having an opening which can be positioned on the patient such that the opening overlies the incision at the operative site. Mini-CABG* retractors are slidably mounted on the base and are provided to spread apart the rib cage halves and engage and retract obstructing tissue. The base may also be provided with surgical instruments which can be used to stabilize or manipulate the heart during surgery.

Once access to the thoracic cavity has been achieved, surgery on the heart to effect valve replacement may be performed. During some procedures, the heart beat is arrested by infusion of a cardioplegic fluid, such as potassium chloride (KCl), to paralyze the myocardium while blood flow circulation is maintained through known heart bypass techniques. Alternatively, the heart is allowed to beat to maintain circulation, while a localized area of the heart, on which surgery is to be performed, is locally immobilized by various instruments.

The heart is incised and the defective valve is cut away leaving a surrounding area of locally tougher tissue. Known heart valve replacement techniques typically include individually passing sutures through the tough tissue by hand to form an array of sutures. Free ends of the sutures are extended out of the thoracic cavity and laid, spaced apart, on the patient's body. The free ends of the sutures are then individually threaded through an edge around the circumference of the replacement valve or a supporting cuff. This is also typically accomplished by hand. Once all sutures have been run through the valve, all the sutures are pulled up taught and the valve is slid or "parachuted" down, by hand, into place adjacent the tough tissue. Thereafter, the replacement valve is secured in place using the sutures. Since the conventional heart valve replacement techniques are exclusively manual procedures, they are typically time consuming and difficult.

Where replacement is performed utilizing an artificial valve, hand held instruments in the form of a stick may be affixed to the valve and used to manipulate the replacement valve into place. The commercially available replacement valves are typically provided with a detachable holder structure which can be engaged by the hand tools.

While the above described procedures are sufficient to successfully secure a heart valve within the heart, they are particularly time consuming. A more suitable apparatus is desired for securing the heart valve in position without the time consuming procedure of passing and tying individual sutures through the valve.

Therefore, a need exists for apparatus and procedures of quickly and efficiently positioning and affixing artificial heart valves within the heart. In particular, an apparatus designed to apply staples which are configured to secure the heart valve to the surrounding tissue and eliminate the need for sutures is desired. The staples may be installed one at a time, or a plurality of staples may simultaneously pierce a cuff of the heart valve.

SUMMARY OF THE DISCLOSURE

There are provided various embodiments of a surgical heart valve stapler and methods for installing a synthetic, artificial heart valve within a patient. A preferred embodiment of the surgical stapler for securing a prosthetic heart valve within a patient generally includes a first cylindrical portion for carrying at least one staple assembly on a distal end thereof A second cylindrical portion is positioned concentrically about the first cylindrical portion and has a camming arm on a distal end thereof, the camming arm being configured to cam the at least one staple assembly radially outward and drive the at least one staple assembly distally such that a first leg of the at least one staple assembly penetrates a cuff of the prosthetic heart valve and a second leg of the at least one staple assembly pierces a portion of heart tissue surrounding the prosthetic heart valve, as the second cylindrical portion is moved distally relative to the first cylindrical portion. A third cylindrical portion is positioned concentrically about the second cylindrical portion and has an anvil flange on a distal end thereof, the anvil flange being configured to crimp the second leg of the at least one staple assembly toward the first leg of the at least one staple assembly to secure the prosthetic heart valve to the surrounding heart tissue as the third cylindrical portion is moved relative to the second cylindrical portion.

Preferably, a plurality of staple assemblies are positioned adjacent a circumference of the distal end of the first cylindrical portion for securing the heart valve to the surrounding heart tissue. The surgical heart valve stapler may further include a fourth cylindrical portion concentrically positioned within the first cylindrical portion for removably engaging a heart valve holder. Additionally, the surgical stapler for securing a prosthetic heart valve within a patient may also include a cylindrical shield portion concentrically interposed the second cylindrical portion and the third cylindrical portion, the cylindrical shield portion dimensioned and configured to shield the at least one staple assembly prior to insertion thereof into the heart valve and heart tissue.

A method of installing a heart valve within a patient is also provided which includes the steps of accessing a site within a heart from which a natural heart valve has been removed; lowering a prosthetic heart valve into position within the site in the heart; positioning a surgical stapler having at least one staple assembly removably held on a distal end thereof adjacent the prosthetic heart valve within the site in the heart; driving a first leg of the at least one staple assembly through a peripheral cuff of the prosthetic heart valve; and crimping a second leg of the at least one staple assembly in a direction toward the first leg such that the second leg pierces a portion of heart tissue surrounding the prosthetic heart valve, thereby securing the prosthetic heart valve to the surrounding heart tissue. The prosthetic heart valve is preferably removably mounted on a distal end of the surgical stapler such that the lowering step and the positioning step are performed simultaneously.

The crimping step in the above method is preferably performed by causing an anvil cylinder disposed on an outer periphery of the surgical stapler to move distally such that a circumferential flange on a distal end of the anvil cylinder crimps the second leg of the at least one staple assembly in a direction toward the first leg. Additionally, the driving step is preferably performed by causing a cylinder within the surgical stapler, having a camming arm on a distal end thereof, to move distally such that the camming arm cams the at least on staple assembly radially outward and drives the at least one staple assembly distally such that a first leg of the at least one staple assembly penetrates a cuff of the prosthetic heart valve and a second leg of the at least one staple assembly pierces a portion of heart tissue surrounding the prosthetic heart valve.

BRIEF DESCRIPTION OF THE DRAWINGS

Various embodiments are described herein with reference to the drawings, wherein.

DETAILED DESCRIPTION OF PREFERRED EMBODIMENTS

Various embodiments are disclosed herein which relate to installation tools and methods for quickly and efficiently positioning and securing a synthetic replacement heart valve within a heart without the necessity of manually suturing the valve in place. The disclosed tools and methods accomplish this objective by providing a stapling apparatus, and method of use thereof, for securing a prosthetic heart valve to a human heart via a plurality of staples secured in a predetermined position within a site in the heart.

Figure 1:
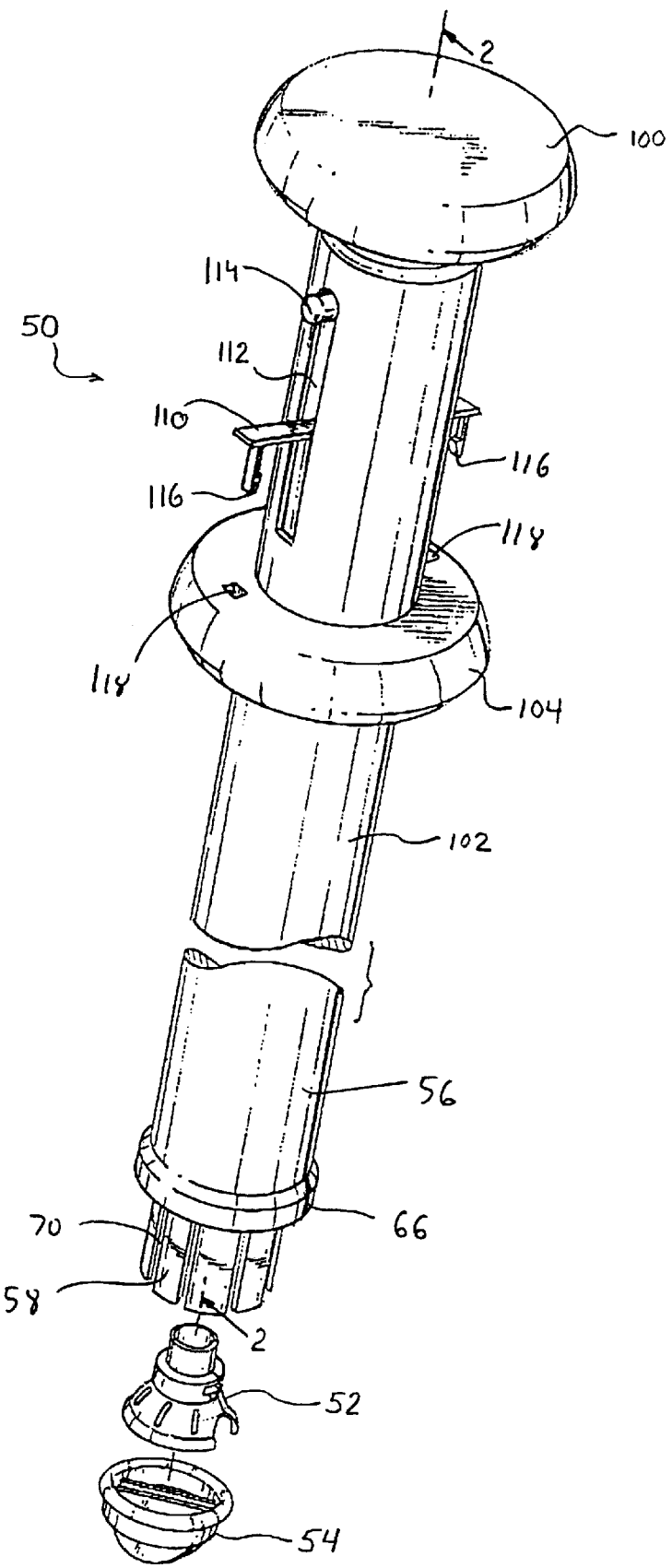
FIG. 1 is a perspective view of a stapling apparatus for use in heart valve replacement surgery in accordance with the present disclosure, and a heart valve assembly.

Referring now to the drawings in detail, and initially to FIG. 1, stapling apparatus 50 in accordance with the present disclosure is illustrated in a perspective view. Stapling apparatus 50 is illustrated in FIG. 1 along with a heart valve holder 52 and a prosthetic heart valve 54. Stapling apparatus 50, heart valve holder 52 and prosthetic heart 54 are detachable from each other.

Stapling apparatus 50 generally includes a knob 100 on a proximal end thereof, a cylindrical body portion 102 and a flange 104 positioned intermediate the proximal and distal ends of cylindrical body portion 102. As used herein, the term "distal" refers to that portion of the assembly, or component thereof, further from the user, while the term "proximal" refers to that part of the assembly, or component thereof, closer to the user. Knob 100 may be held or depressed by the user to restrain or move certain of the components within cylindrical body 102 as will be discussed in further detail below. Cylindrical body 102 includes a plurality of individual cylindrical portions as will be discussed in further detail below.

Figure 2:
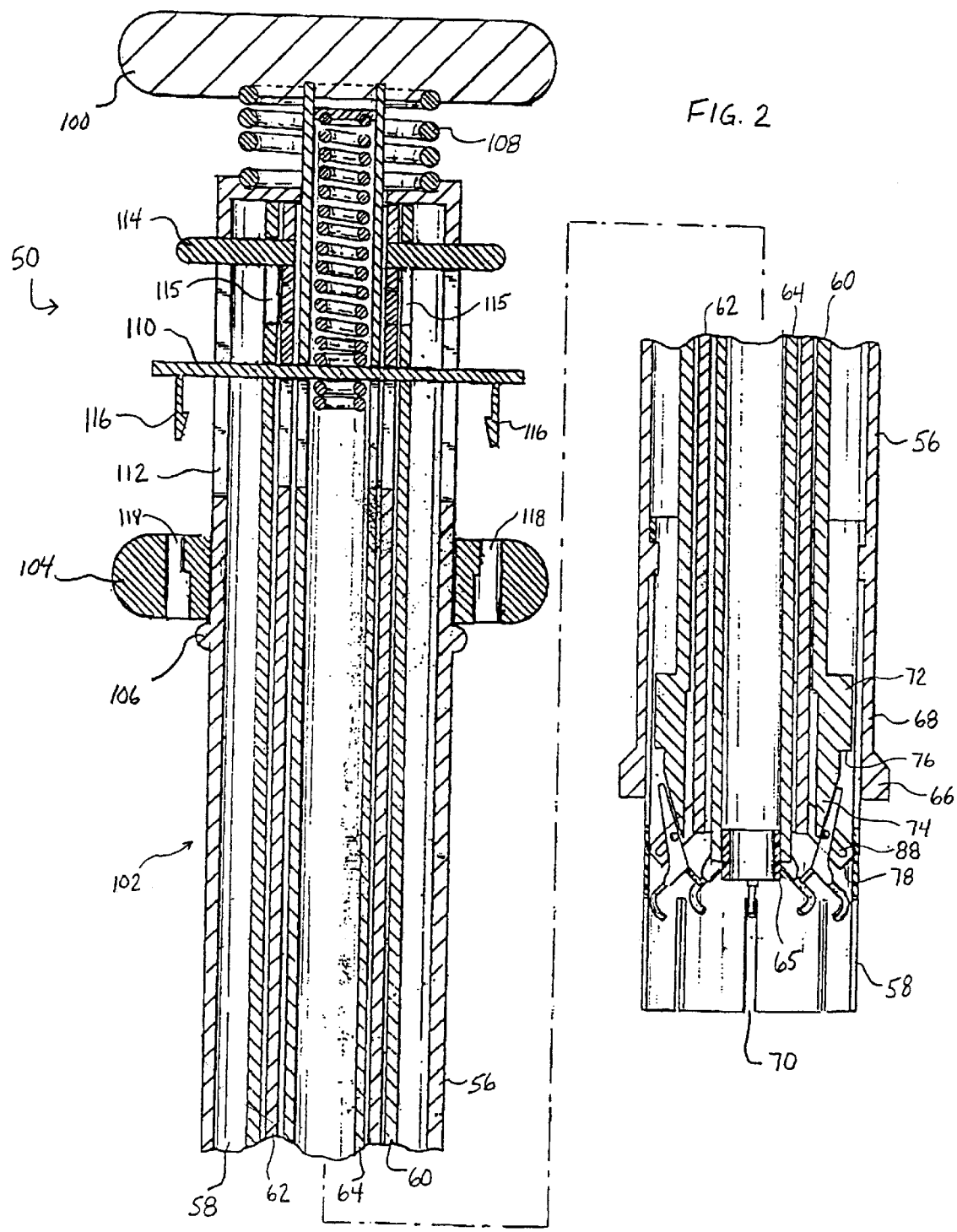
FIG. 2 is a cross-sectional view of the stapling apparatus taken along lines 2—2 of FIG. 1.

Flange 104 is slidably mounted on an outer surface of cylindrical body 102. As illustrated in FIG. 2, flange 104 is restrained from sliding distally along cylindrical body 102 by a fixed circumferential flange 106 on the outer periphery of cylindrical body 102.

Referring to FIG. 2, stapling apparatus 50 is shown in a cross-sectional view to illustrate the components therein. Stapling apparatus 50 generally includes a series of concentric cylinders designed to insert a prosthetic heart valve in a predetermined location within a heart, and secure the heart valve to the heart via staples at the predetermined location. More specifically, the cylinders within stapling apparatus 50, described from the outside to the inside, include an anvil cylinder 56, a shield cylinder 58, a camming arm cylinder 60, a staple carrier cylinder 62 and a heart valve holder cylinder 64.

Anvil cylinder 56 is the outermost cylinder of stapling apparatus 50 and includes a circumferential flange 66 on a distal end 68 thereof. As discussed above, anvil cylinder 56 also includes a fixed circumferential flange 106 on the outer periphery thereof to restrain flange 104 from moving distally. Anvil cylinder 56 also includes two longitudinal slots 112 formed in a proximal portion thereof to facilitate relative sliding motion of camming arm cylinder 60 and staple carrier cylinder 62, as will be discussed in further detail below. A circular recess is formed in a proximal end of anvil cylinder 56 to receive a distal end of a spring 108.

Shield cylinder 58 is positioned inside and adjacent anvil cylinder 56 and functions to shield the staples and heart valve as they are initially lowered into position within the void in the heart. Shield cylinder 58 includes a plurality of slots 70 formed in a distal end thereof. The plurality of slots 70 are configured and dimensioned corresponding to the number and size of staples at the distal end of staple carrier cylinder 62. Slots 70 allow the staples to move radially outward prior to being forced through a cuff of the prosthetic heart valve, as will be discussed in further detail below.

Camming arm cylinder 60 includes an elongate cylindrical portion having a camming arm 72 attached to a distal end thereof. Camming arm 72 includes a ramp portion 74 and a shoulder 76, each of which sequentially engage an arm of a staple to cam the staple radially outward and push the staple through a cuff of a heart valve, as will be discussed in further detail below. Camming arm cylinder 60 further includes two arms 110 extending from a proximal portion thereof to facilitate movement of camming arm cylinder 60 by a user. Arms 110 extend radially outward from cylinder 60 through slots 112 formed in anvil cylinder 56. Arms 110 include two tabs 116 extending distally therefrom. Tabs 116 include sloped distal portions such that upon insertion into bores 118 formed in flange 104 tabs 116 are resiliently cammed outwardly until they snap into position within bores 118 to hold arms 110 in a fixed position relative to flange 104.

Staple carrier cylinder 62 includes an elongate cylindrical portion having a plate 78 extending from a distal end thereof at an angle of approximately 45 degrees. Plate 78 has a slot 88 formed longitudinally along a central axis thereof to slidably engage the staples. Staple carrier cylinder 62 further includes two arms 114 extending from a proximal portion thereof to facilitate movement of staple carrier cylinder 62 by a user. Arms 114 extend radially outward from cylinder 62 through slots 112 formed in anvil cylinder 56 and slots 115 formed in camming arm cylinder 60.

Heart valve holder cylinder 64 is the central most cylinder within stapling apparatus 50 and includes a cylindrical portion 65 extending from a distal end thereof which is configured and dimensioned to removably engage valve holder 52 to facilitate positioning of heart valve 54 within the predetermined position within a heart.

The method of inserting and stapling a prosthetic heart valve within a heart with the presently disclosed stapler will now be discussed with reference to FIGS. 2–10. Access to the heart through the thoracic cavity is accomplished using well known surgical procedures. For example, an incision is made through the sternum of a patient to access the thoracic cavity and expose the heart. Preferably, access to the cavity is maintained with the assistance of a retractor, such as, for example, the Mini-CABG* retractor and related accessories available from United States Surgical Corporation, Norwalk, Conn. The retractor generally includes an oval planar base and is positioned on the patient such that an opening defined by the base overlies the incision. A plurality of retractor blades are slidably mounted on the base and engage and retract the tissue edges of the incision. Optionally, additional instruments may be affixed to the base to manipulate and/or stabilize the heart to facilitate surgery thereon. Blood flow circulation may be maintained using known techniques. Thus, access to the heart is achieved and maintained. Other known open surgical procedures to access the heart are also contemplated and may be substituted for the procedure described herein. Once access to the heart has been obtained, the heart is opened and a dysfunctional valve is removed using known surgical procedures.

Figure 3:
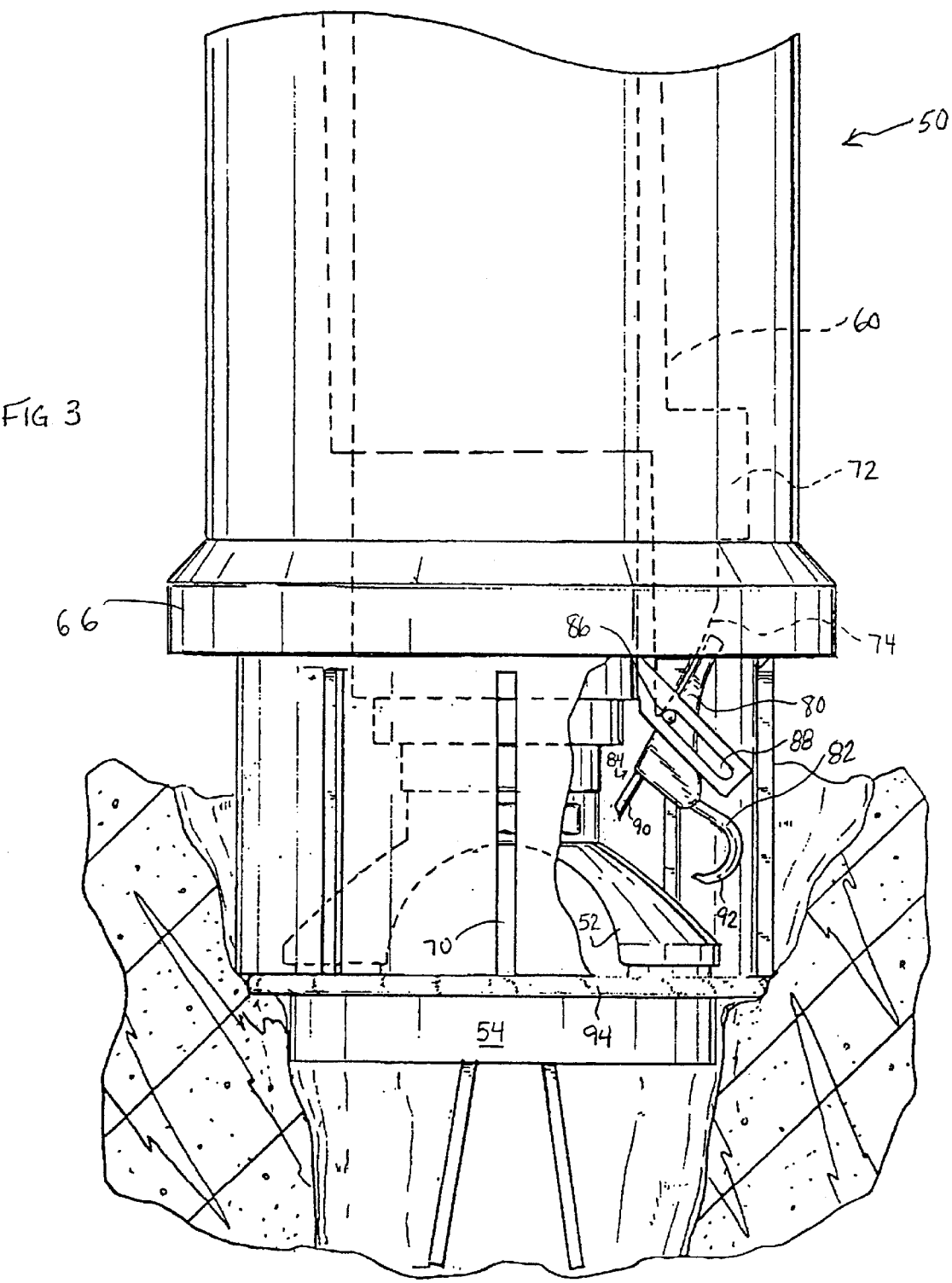
FIG. 3 is a partial cross-sectional side view of the distal end of the stapling apparatus of FIG. 1 partially within a thoracic cavity in its initial position adjacent the heart valve.

Continuing now with the description of a method of inserting and stapling a prosthetic heart within the heart and referring initially to FIG. 3, the distal end of stapling apparatus 50, having heart valve holder 52 and heart valve 54 attached thereto, is placed within the void in the heart created by the removal of the dysfunctional heart valve. Typically, following removal of a dysfunctional heart valve, the heart tissue in the surrounding area is tougher than the remainder of the heart tissue and is therefore amenable to retaining staples. Once the stapling apparatus 50 is properly positioned, camming arm cylinder 60 is moved distally by pushing on arms 110 (see FIG. 2) such that ramp portion 74 of camming arm 72 engages an arm portion 80 of a staple assembly 84. In response to the engagement with ramp portion 74, staple assembly 84 is forced to pivot about pin 86 in guide slot 88.

Figure 4:
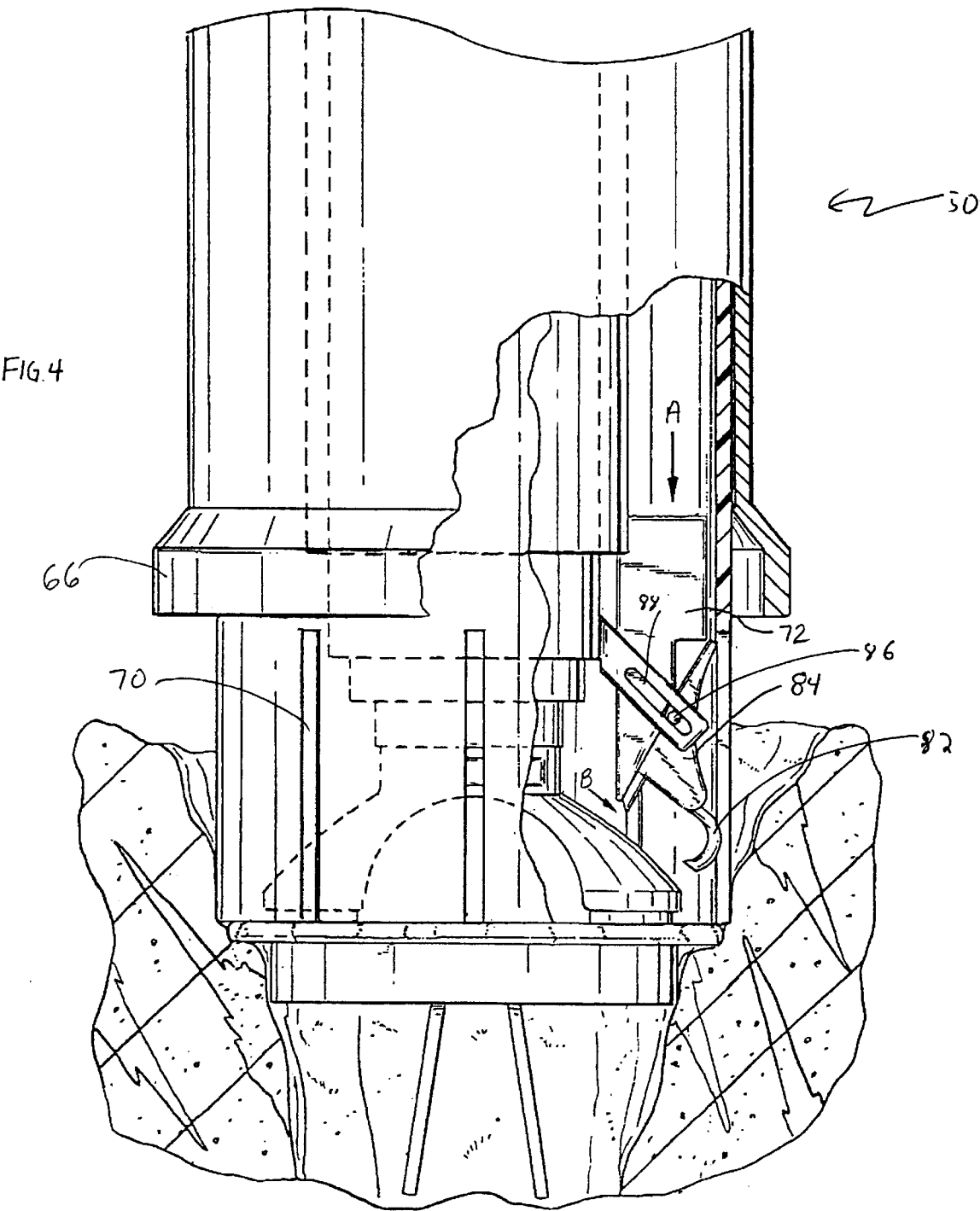
FIG. 4 is a partial cross-sectional side view of the stapling apparatus of FIG. 1 partially within the thoracic cavity and driving the staple out.
Figure 5:
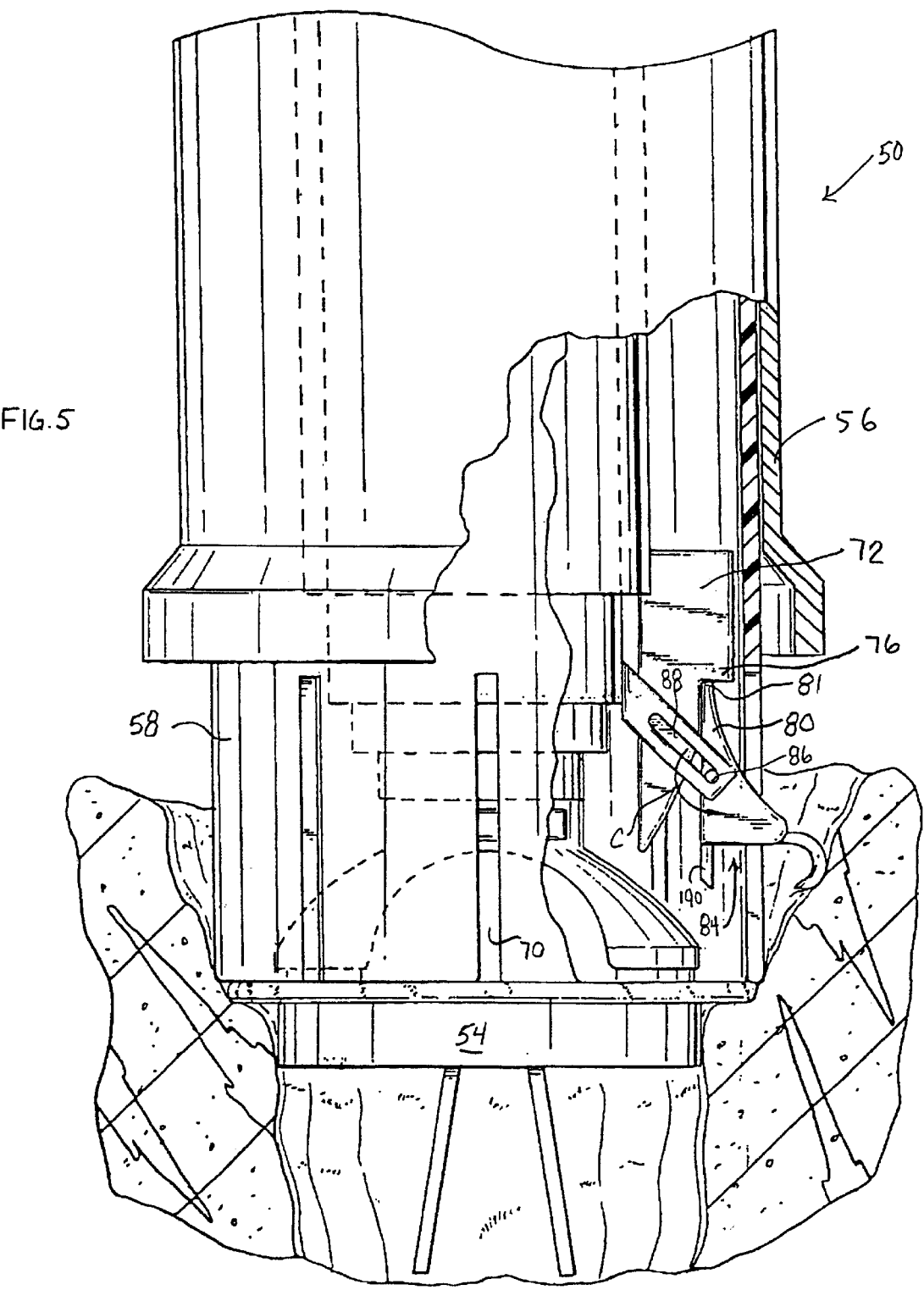
FIG. 5 is a partial cross-sectional side view of the stapling apparatus of FIG. 1 partially within the thoracic cavity with the staple in position to pierce tissue.

The continued distal movement of camming arm 72 in the direction of arrow A illustrated in FIG. 4 forces staple assembly 84 radially outward along the axis of guide slot 88, as indicated by arrow B. As illustrated in FIG. 5, once pin 86 reaches the end of its travel within guide slot 88, staple assembly 84 will rotate about pin 86 to a position which is parallel to the longitudinal axis of stapling apparatus 50, as indicated by arrow C. A proximal tip 81 of arm portion 80 is now positioned against the shoulder 76 of camming arm 72, and a portion of staple assembly 84 extends through a corresponding slot 70 in shield 58.

Figure 6:
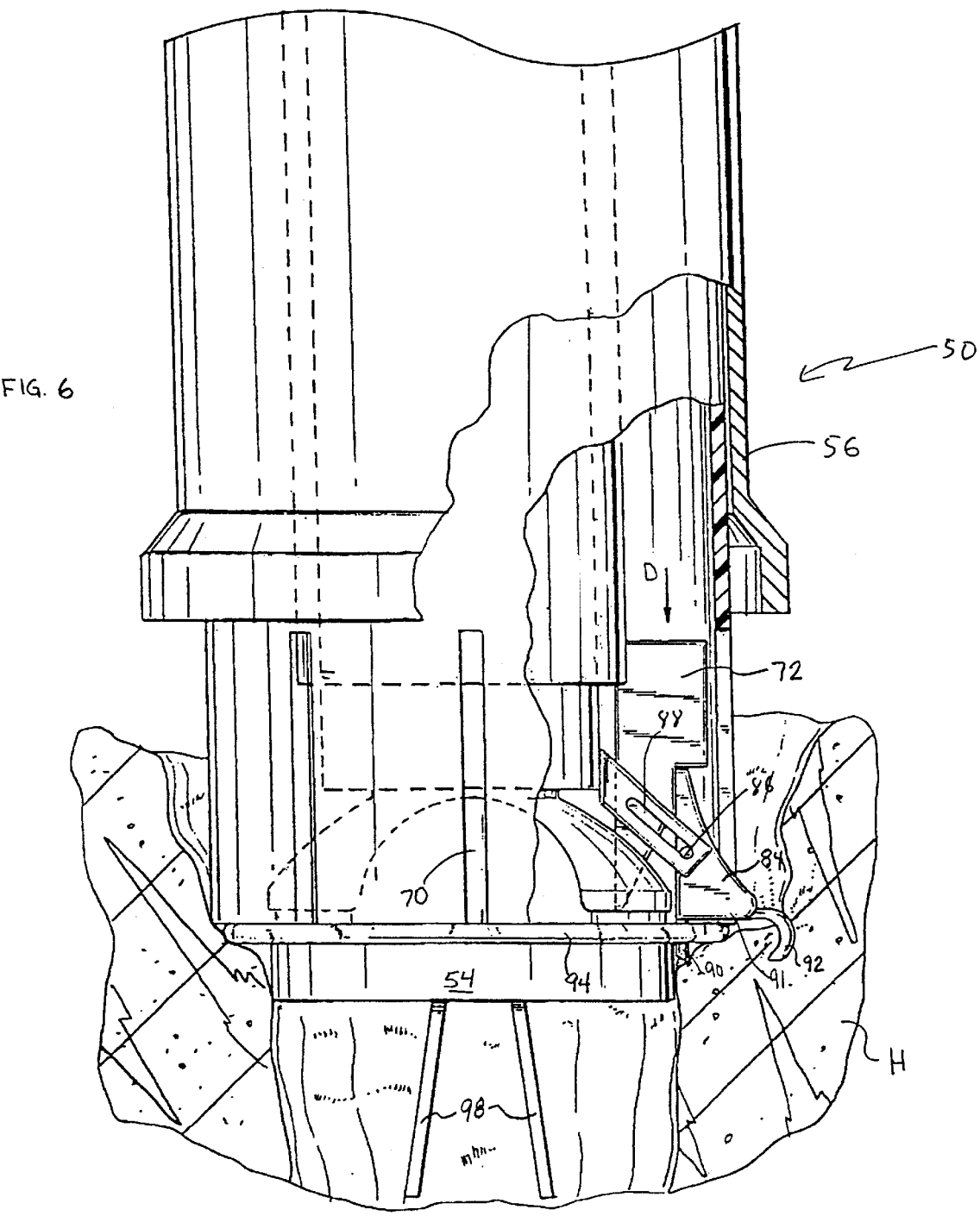
FIG. 6 is a partial cross-sectional side view of the stapling apparatus of FIG. 1 partially within the thoracic cavity with a staple piercing the heart tissue and cuff of the heart valve.

Referring now to FIG. 6, the continued distal motion of camming arm 72 will drive staple assembly 84 distally in the direction indicated by arrow D. Staple assembly 84 is preferably formed as a one-legged staple wherein the staple is formed with a first end having a straight leg 90, a second end having a curved substantially C-shaped leg 92 and a back span 91 connecting legs 90 and 92. The concave portion of leg 92 opens toward the straight leg 90. As camming arm 72 drives staple assembly 84 distally, straight leg 90 is forced to pierce a cuff 94 of heart valve 54. Leg 92 is simultaneously forced to penetrate a toughened portion of the heart tissue H surrounding heart valve 54. Staple assembly 84 is now in position to be crimped to secure heart valve 54 in place. Heart valve assembly 54 typically includes valve cuff 94 and a valve ring 96 having a plurality of valve leaflets 98 pivotally mounted therein. The heart valve ring 96 is generally formed by molding or machining a suitable biocompatible material such as, for example, stainless steel. Valve cuff 94 is preferably formed of a permeable felt, to facilitate penetration thereof by staple legs 90.

Figure 7:
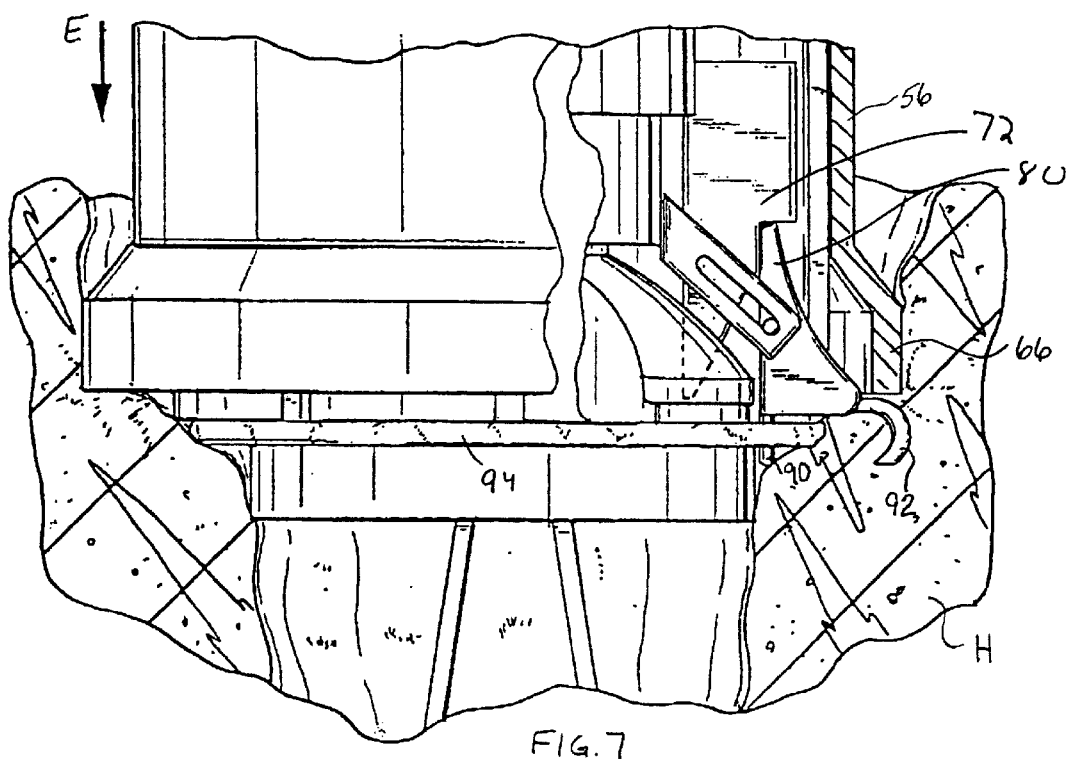
FIG. 7 is a partial cross-sectional side view of the stapling apparatus of FIG. 1 partially within the thoracic cavity illustrating the initial staple crimping operation.
Figure 8:
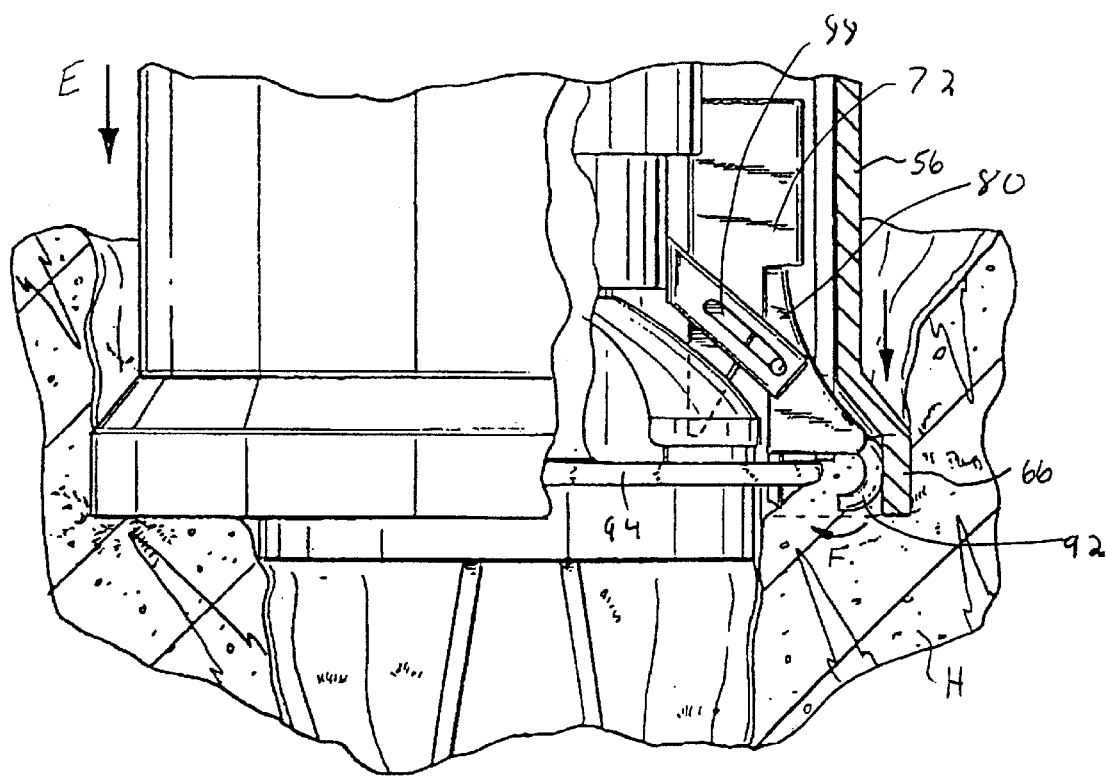
FIG. 8 is a partial cross-sectional side view of the stapling apparatus of FIG. 1 partially within the thoracic cavity to illustrate the staple crimping operation.

Referring now to FIGS. 7 and 8, the staple crimping operation is illustrated. To begin the crimping operation, anvil cylinder 56 is moved distally, in the direction indicated by arrow E, until a distal end of circumferential flange 66 contacts leg 92 of staple assembly 84 as shown in FIG. 7. As anvil cylinder 56 continues to move distally, circumferential flange 66 forces leg 92 to bend inward toward leg 90 as indicated by arrow F in FIG. 8. As leg 92 is bent toward leg 90, it pierces and encases a portion of heart tissue H between the two legs of staple assembly 84 to thereby secure heart valve 54 to the surrounding heart tissue H.

Figure 9:
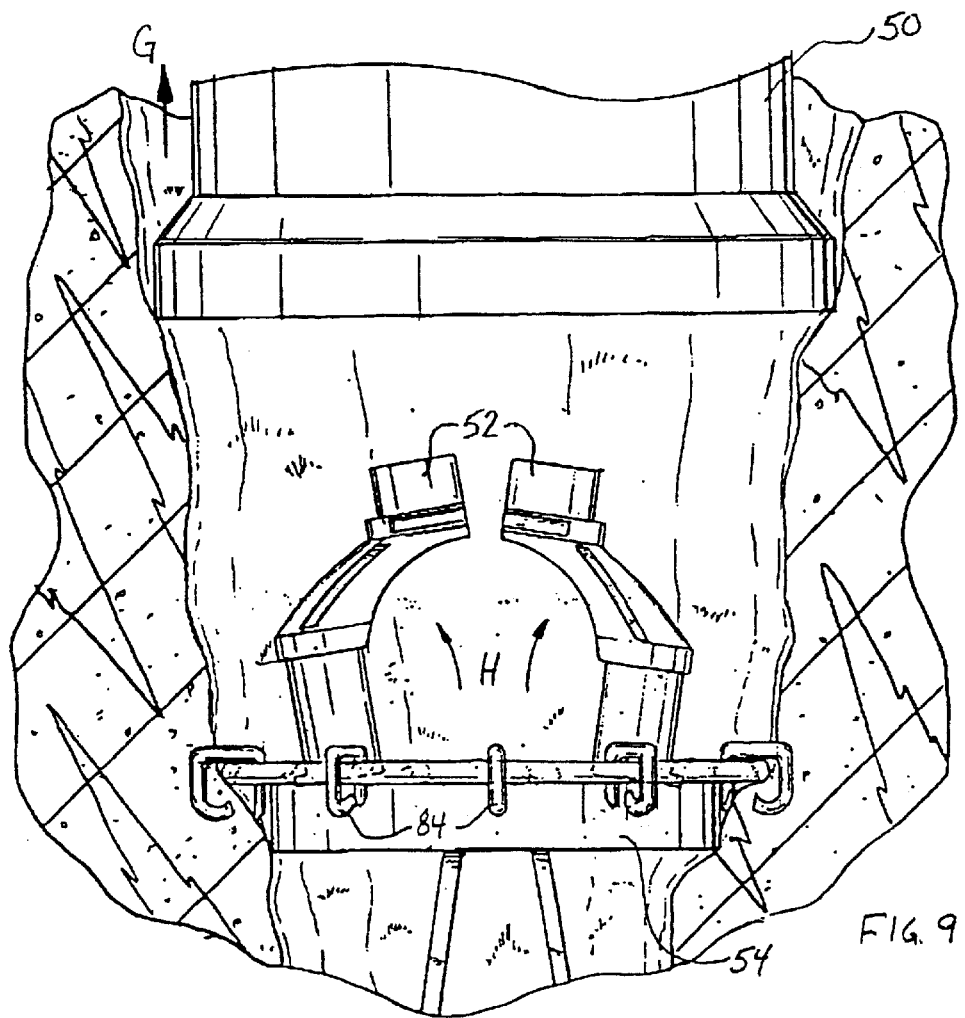
FIG. 9 is a view illustrating the removal of the stapling apparatus and heart valve holder from a heart valve.
Figure 10:
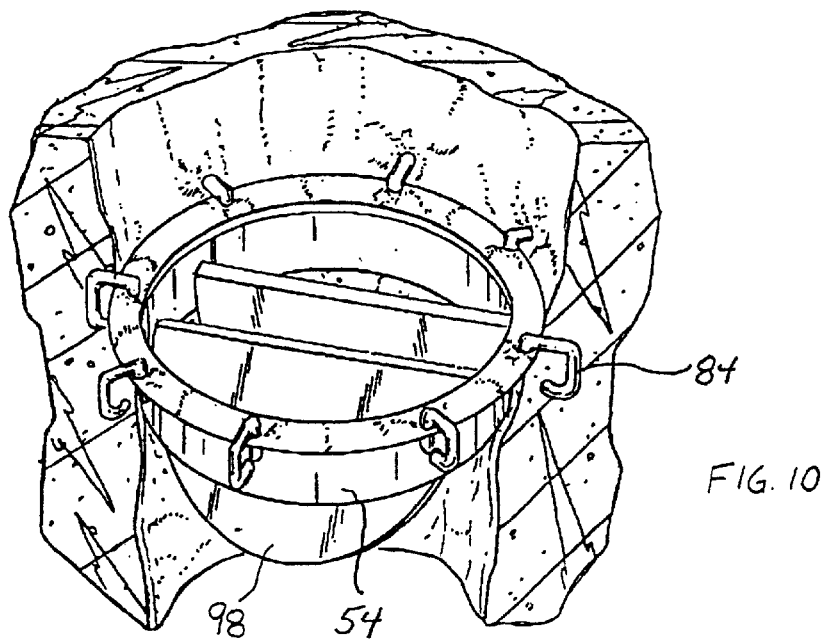
FIG. 10 is a perspective view of a heart valve secured within a bore of a heart.

Referring now to FIGS. 9 and 10, with the heart valve 54 secured via staples 84 to heart tissue H, stapling apparatus 50 is detached from heart valve holder 52 and is removed therefrom in the direction indicated by arrow G. Once stapling apparatus 50 is removed, heart valve holder 52, which is formed in two half sections, is similarly removed as illustrated by arrows I. The heart valve installation procedure is now complete and the heart valve is illustrated secured to the heart tissue H in FIG. 10. The thoracic cavity may now be closed using known surgical techniques.

It will be understood that various modifications may be made to the embodiments disclosed herein. For example, it is noted that variously dimensioned heart valve assemblies or stapling apparatus may be provided to facilitate replacement of corresponding heart valves. Therefore, the above description should not be construed as limiting but merely as exemplifications of preferred embodiments. Those skilled in the art will envision other modifications within the scope and spirit of the claims appended hereto.

What is claimed is:

1. A surgical stapling system for securing a prosthetic heart valve within a patient comprising:

a prosthetic heart valve having a cuff; and a surgical stapler including at least two concentric cylinders configured to move along a common longitudinal axis and relative to each other, the at least two concentric cylinders further configured to carry at least one staple assembly on a distal end thereof and to drive the at least one staple assembly in a direction such that a first leg of the at least one staple assembly penetrates the cuff of the prosthetic heart valve and at least a first portion of the surrounding heart tissue and a second leg of the at least one staple assembly penetrates a second portion of heart tissue surrounding the prosthetic heart valve, the surgical stapling system being configured and dimensioned to position the second leg of the at least one staple assembly in a substantially radial direction from the first leg of the at least one staple assembly to secure the prosthetic heart valve to the surrounding heart tissue.

2. The surgical stapling system in claim 1, wherein the at least two cylinders are further configured to crimp the second leg of the at least one staple assembly toward the first leg of the at least one staple assembly to secure the prosthetic heart valve to the surrounding heart tissue.

3. The surgical stapling system in claim 1, wherein the at least two cylinders are further configured to removably engage a heart valve holder.

4. A surgical stapler comprising:

a first cylindrical assembly for carrying at least one staple assembly on a distal end thereof;

a second cylindrical assembly positioned concentrically about said first cylindrical assembly;

said first and second cylindrical assemblies configured to move along a common longitudinal axis and relative to each other;

said second cylindrical assembly including a camming arm and being configured and dimensioned to be repositionable from a first position to a second position, wherein in the first position the camming arm is positioned separate from the at least one staple assembly and in the second position the camming arm is repositioned to move the at least one staple assembly.

5. The surgical stapler of claim 4, wherein the at least one staple assembly has a first leg and a second leg and the camming arm is configured and dimensioned to move at least one leg of the staple assembly.

6. The surgical stapler of claim 4, wherein the at least one staple assembly is moved by the camming arm in a radial direction.

7. The surgical stapler of claim 6, wherein the at least one staple assembly is moved by the camming arm in a radial direction towards the center of the surgical stapler.

8. A surgical stapler for securing a prosthetic heart valve within a patient comprising:

at least two concentric cylinders configured to move along a common longitudinal axis and relative to each other, the at least two concentric cylinders further configured to carry at least two staple assemblies on a distal end thereof and to drive the at least two staple assemblies in a direction such that a first leg of each said staple assembly penetrates a cuff of the prosthetic heart valve and a second leg of each said staple assembly pierces a portion of heart tissue surrounding the prosthetic heart valve to secure the prosthetic heart valve to the surrounding heart tissue, wherein the at least two staple assemblies are substantially diametrically opposed to each other, wherein the at least two cylinders are further configured to removably engage a heart valve holder.

* * * * *